US00RE36092E

United States Patent [19]

König et al.

[11] E Patent Number: Re. 36,092

[45] Reissued Date of Patent: Feb. 9, 1999

[54] SUBSTITUTED CYCLODEXTRINS AND PROCESS FOR CHROMATOGRAPHIC SEPARATION OF CHIRAL ORGANIC COMPOUNDS

[75] Inventors: Wilfried König, Pinneberg; Gerhard Wenz, Mainz; Sabine Lutz, Hamburg; Eva von der Bey, Mainz, all of Germany

[73] Assignee: Macherey-Nagel & Co., Duren-Rolsdorf, Germany

[21] Appl. No.: 526,141

[22] PCT Filed: Mar. 25, 1989

[86] PCT No.: PCT/EP89/00332

§ 371 Date: Dec. 3, 1990

§ 102(e) Date: Dec. 3, 1990

[87] PCT Pub. No.: WO89/09235

PCT Pub. Date: Oct. 5, 1989

Related U.S. Patent Documents

Reissue of:

[64] Patent No.: 5,198,429
Issued: Mar. 30, 1993
Appl. No.: 585,117
Filed: Dec. 3, 1990

U.S. Applications:

[63] Continuation of Ser. No. 189,361, Dec. 30, 1993, abandoned.

[30] Foreign Application Priority Data

Mar. 30, 1988 [DE] Germany ..... 38 10 737.6

[51] Int. Cl.[6] ..... C08B 37/16; C07B 63/00

[52] U.S. Cl. ..... 514/58; 536/103; 435/280; 562/401; 210/632; 210/634; 210/635; 210/636

[58] Field of Search ..... 514/58; 536/103; 435/280; 562/401; 210/632, 634, 635, 636

[56] References Cited

U.S. PATENT DOCUMENTS

| | | | |
|---|---|---|---|
| 4,582,900 | 4/1986 | Brandt et al. | 536/103 |
| 4,590,167 | 5/1986 | Gunther et al. | 436/162 |
| 5,078,886 | 1/1992 | Hsu | 562/401 |

FOREIGN PATENT DOCUMENTS 0146841 7/1985 European Pat. Off. .

OTHER PUBLICATIONS

Chemical Abstracts, vol. 109, Oct. 10, 1988 Abstract 109:125206x.

Tetrahedron, vol. 39, No. 9, 1983 Pergamon Press Ltd. (Oxford, GB), A.P. Groft et al.: "Synthesis of Chemically Modified Cyclodextrans", pp. 1417, 1427–1433, 1472, see p. 1431.

Starch/Stärke, vol. 39, No. 10, Oct. 1987, VCH Verlagsgesellschaft mbH (Weinheim, DE), J. Szejth: "Application of Cyclodextrins in the Chromatography", pp. 357–362, see p. 358.

*Primary Examiner*—John Kight
*Assistant Examiner*—Everett White
*Attorney, Agent, or Firm*—Sprung Kramer Schaefer & Briscoe

[57] ABSTRACT

Substituted cyclodextrins of the general formula in which $R^2$ and $R^6$ mean straight-chain or branched alkyl or alkenyl groups with 1 to 8 carbon atoms or cycloalkyl groups with 5 to 8 carbon atoms which can be the same or different, and $R^3$ represents a straight-chain or branched alkyl or alkenyl group, which can be the same or different to the residues $R^2$ and $R^6$, with 1 to 8 carbon atoms or a cycloalkyl group with 5 to 8 carbon atoms, or an acyl group with an optionally substituted, saturated or olefinically unsaturated aliphatic or cycloaliphatic or with an aromatic hydrocarbon residue with 1 to 8 carbon atoms, and n=6 or 7, a process for their production, and a process for the separation of chiral organic compounds by chromatographic separation processes in which the substituted cyclodextri are used as stationary phase.

15 Claims, 6 Drawing Sheets

Figure 1:
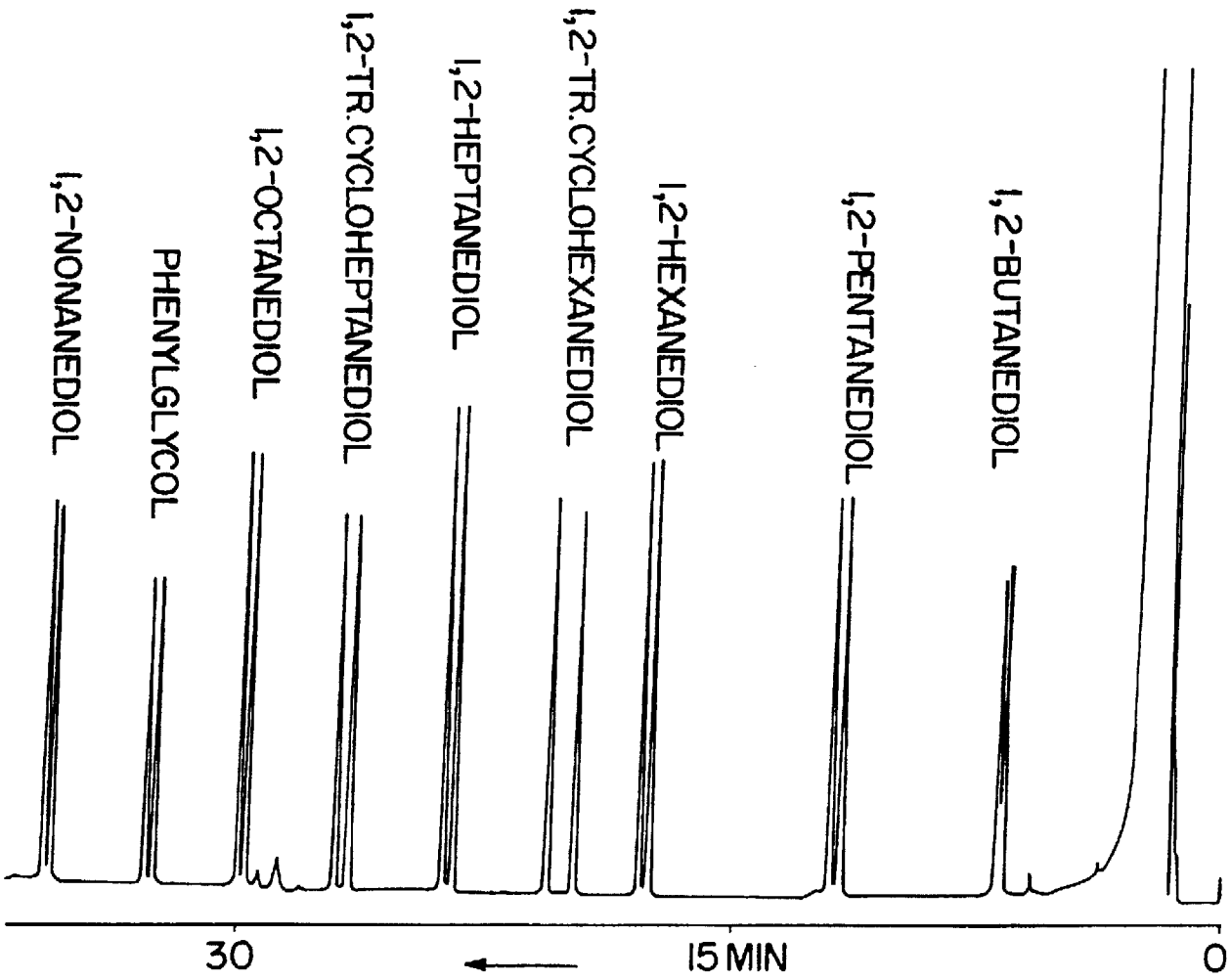

SUBSTITUTED CYCLODEXTRINS AND PROCESS FOR CHROMATOGRAPHIC SEPARATION OF CHIRAL ORGANIC COMPOUNDS

Matter enclosed in heavy brackets [ ] appears in the original patent but forms no part of this reissue specification; matter printed in italics indicates the additions made by reissue.

*This application is a continuation of application Ser. No. 08/189,361, filed on Dec. 30, 1993, now abandoned which is a Reissue application of Ser. No. 07/585,117, filed on Dec. 30, 1990, now U.S. Pat. No. 5,198,429.*

The present invention relates to substituted cyolodextrins, to a process for their production, and to a process for the separation of chiral organic compounds by chromatographic separation processes, particularly gas chromatography, using the substituted cyclodextrins as stationary phase.

Substituted cyclodextrins are known, for example, from DE-OS 37 10 569, which is no prior publication, which describes the production of ultrathin films from these cyclodextrin compounds or an inclusion compound on the basis of the cyclodextrin compounds. These ultrathin films can be used, for example, as protective film for compounds which are sensitive to light and oxygen, or as carrier in chromatography.

Triethyl-β-cyclodextrin is described in Journal of Pharmaceutical Sciences (1987, 660). An alkyl-acyl-compound ($R_2$=$R_6$=methyl, $R_3$=benzoyl, n=7, of the following general formula) is described in J. Chem. Soc. Perkin Trans. (1987), 1323.

Single cyclodextrin derivatives were also mentioned as possible stationary phases, however, realization of this possibility was limited due to the properties of the known substances, this is described, for example, in ACS Symposium Series, 1987, vol. 342, pages 200 to 217, and in Starch/Starke, 1987, pages 357 to 358.

Up to now, the separation of enantiomeric, low-molecular chiral compounds by gas-chromatography has been conducted by using chiral low-molecular or polymeric separation phases with amide or diamide structure.

Such a separation is almuost exclusively limited to enantiomers with amide, carbamate, oxime, or hydroxyl groups. In this connection, intermolecular hydrogen bridge bonds are built so that diastereomeric associates between chiral separation phase and chiral substrates are formed.

In order to improve the separation results, the enantiomers to be separated were mostly converted into derivatives with amide or carbamoyl functions.

Due to the fact that the formed derivatives are difficultly volatile, high operating temperatures of the chromatographic columns are required and thus leads to uneven courses of the base-lines of the chromatrograms and to reduced separation efficiency due to cross diffusion.

It was the object of the present invention to provide improved stationary phases for the separation of chiral compounds, particularly of enantiomers, and a process for the separation of chiral compounds.

Surprisingly,it was found that this object is achieved by substituted cyclodextrins of the general formula:

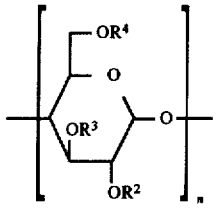

in which:

$R^2$ and $R^6$ mean straight-chain or branched alkyl or alkenyl groups with 1 to 8 carbon atoms or cycloalkyl groups with 5 to 8 carbon atoms which can be the same or different, and $R^3$ represents a straight-chain or branched alkyl or alkenyl group, which can be the same or different to the residues $R^2$ and $R^6$, with 1 to 8 carbon atoms or a cycloalkyl group with 5 to 8 carbon atoms, or an acyl group with an optionally substituted, saturated or olefinically unsaturated aliphatic or cycloaliphatic or with an aromatic hydrocarbon residue with 1 to 8 carbon atoms, and n=6 or 7, whereby compounds with $R^2$=$R^3$=$R_6$=methyl, n=6 or 7

$R^2$=$R^3$=$R_6$=ethyl, n=7

$R^2$=$R^6$=allyl, $R^3$=methyl, n=7

$R^2$=$R^6$=prop-1-enyl, $R^3$=methyl, n=7

$R^2$=$R^6$=methyl, $R^3$=n-butyl, n=7

$R^2$=$R^6$=methyl, $R^3$=benzoyl, n=7 and $R^2$=$R^3$=alkyl or acyl, $R^6$=C>$_4$-alkyl are excluded.

A further solution. of the problem underlying the present invention is the provision of a process for the chromatographic separation of chiral compounds, particularly of enantiomers.

In this connection, compounds with $R^2$=$R^3$=$R^6$=methyl, n=6 or 7

$R^2$=$R^6$=allyl, $R^3$=methyl, n=7

$R^2$=$R^6$=prop-1-enyl, $R^3$=methyl, n=7

$R_2$=$R^6$=methyl, $R^3$=n-butyl, n=7 are excluded.

The substituted cyclodextrins according to the present invention permit a separation of enantiomers which is mainly caused by inclusion effects at the macrocyclic chiral cyclodextrins, and which—due to the separation mechanism which, compared to the separation phases according to the prior art, is completely different—can be employed even for tho se enantiomers not being able to form hydrogen bridges and therefore could not be separated on the chiral separating phases used until now.

For the use as separation phases in gaselhromatography the compounds according to the present invention on the one hand have the advantage of having a very high temperature stability of more than 200° C., on the other hand, the separation mechanism which—compared to the separation phases known until now—is different in most cases permits the conversion into very readily volatile derivatives, such as trifluoroacetylated compounds, which in case of correspondingly low temperatures are cluted from the column.

Those compounds in which the residues $R^2$, $R^3$ and $R^6$ are alkyl or alkenyl groups with 3 to 6 carbon atoms and/or $R^3$ means the acetyl group are particularly preferred from the series of compounds according to the present invention of the O-peralkylated α- and β-cyclodextrin derivatives and those in which the hydroxyl groups of the cyclodextrin are alkylated in the 2- and 6-position of the glucose units and the hydroxyl group is acylated in 3-position.

Particularly preferred are the substituted cyclodextrins consisting of 6 or 7 glucose rings and having as substituents $R^2$, $R_3$ and $R^6$ the n-pentyl-group or as substituent $R^3$ the acetyl group and as $R^2$ and $R^6$ n-pentyl groups.

The products according to the present invention are produced in that at first α- or β-cyclodextrin is dissolved in an anhydrous solvent and reacted with an alkyl halide under addition of powdered alkali hydroxide. This reaction stage can be conducted in such a way that optionally either the hydroxyl groups in 2 or 6-position or the three hydroxyl groups being in 2-, 3-, and 6-position are alkylated.

The 2,6-di-O-alkylated intermediate product is optionally isolated and reacted in an anhydrous solvent with an acylating agent, preferably an acid anhydride or an acid chloride, under the addition of a tertiary amine.

The crude products respectively obtained can be purified by column chromatography and isolated in pure form. The characterization was carried out by $^1$H- and $^{13}$C-nuclear resonance spectroscopy, respectively, and by chemical degradation with subsequent analysis of the degradation products by combined gas chromatography and mass spectrometry according to P. MischnickLübbecke, W. A. König and M. Radeloff, Starch/Stärke 39 (1987) 425.

Coating of the separating capillary columns with the substituted cyclodextrins according to the present invention is carried out according to W. A. König and K. Ernst, J. Chromatogr. 280 (1983) 135.

The capillaries filled with the separating phases according to the present invention are particularly suitable for the separation of, for example, enantiomers of diols, polyols, monosaccharides, methylglycosides, 1,5-anhydroalditols, hydroxy esters, alcohols, aldols, lactones, spiro acetals, amino alcohols, amines, amino-acid esters, and other chiral compounds which, if necessary, are trifluoroacetylated with trifluoroacetic acid anhydride in dichloromethane according to known processes and thus can be converted into volatile derivatives suitable for gas-chromatography.

Glass or "fused-silica"-capillary columns having a length of 25 m, 40 m, or 50 m were filled with the separation phases according to the present invention. FIGS. 1 to 10 demonstrate exemplary separations of enantiomers on the separating phases hexakis(2,3,6-tri-O-pentyl)-α-cyclodextrin (FIGS. 1 to 5 and 9), hexakis(2,6-di-O-pentyl-3-O-acetyl)-α-cyclodextrin (FIG. 10) and heptakis(2,6-di-O-pentyl-3-O-acetyl)-β-cyclodextrin (FIGS. 6 to 8), respectively. The Figures clearly show the even baseline of the chromatograms and the excellent separation efficiency of the separating columns filled with the substituted cyclodextrins according to the present invention.

The following exemplary separations are shown by the individual Figures:

FIG. 1: Separation of enantiomers of a mixture of racemic diols after trifluoroacetylation, 40 m-glass capillary with hexakis(2,3,6-tri-O-pentyl)-α-cyclodextrin; 48° C., 5 min. isothermal, then 2°/min.

Figure 2:
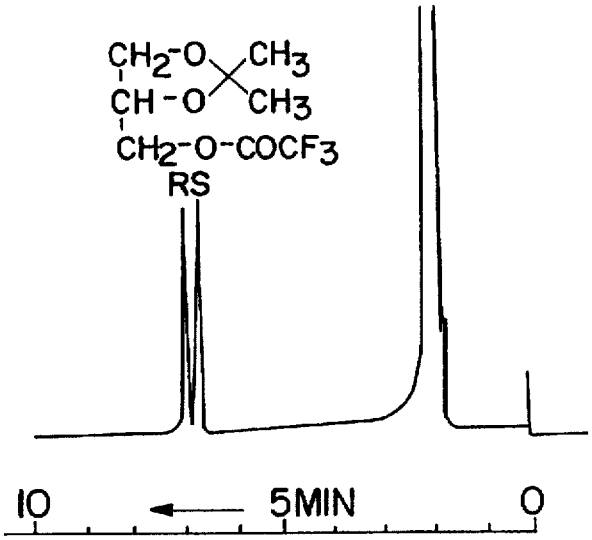

FIG. 2: Separation of enantiomers of isopropylidene glycerol after trifluoroacetylation. 40 m-glass capillary with hexakis(2,3,6-tri-O-pentyl)-α-cyclodextrin; 70° C.

Figure 3:
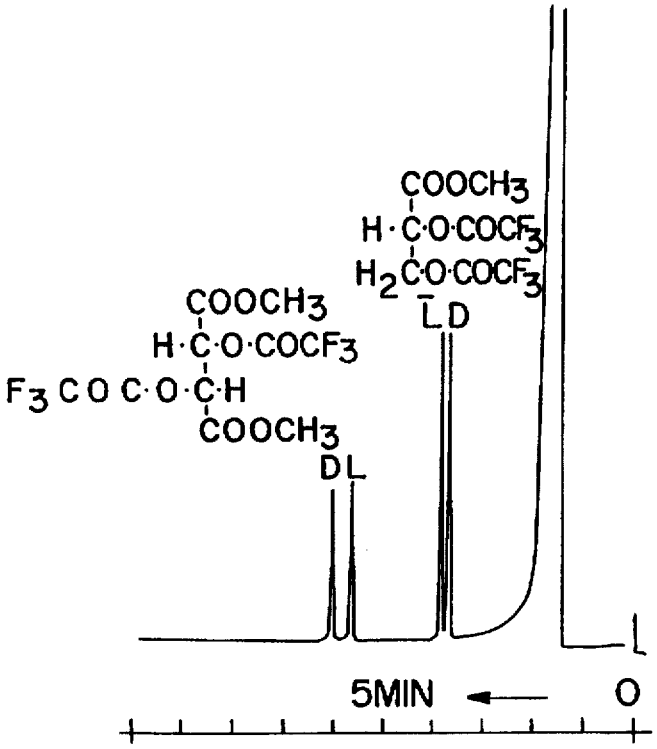

FIG. 3: Separation of enantiomers of glyceric acid and tarric acid after esterification with methanolic HCl and trifluoroacetylation; 40 m-glass capillary with hexakis(2,3,6-tri-O-pentyl)-α-cyclodextrin; 90° C.

Figure 4:
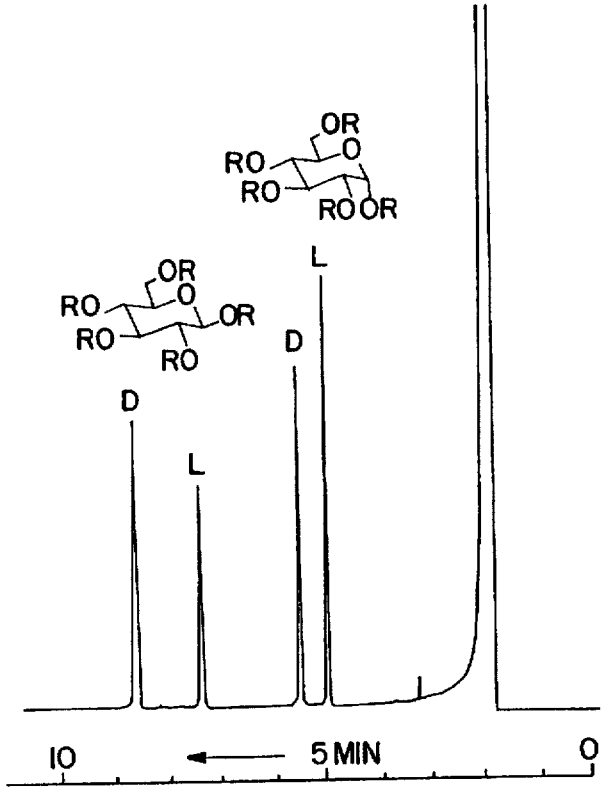

FIG. 4: Separation of enantiomers of D- and L-glucose after trifluoroacetylation. 40 m-hexakis(2,3,6-tri-O-pentyl)-α-cyclodextrin-glass-capillary; 115° C.

Figure 5:
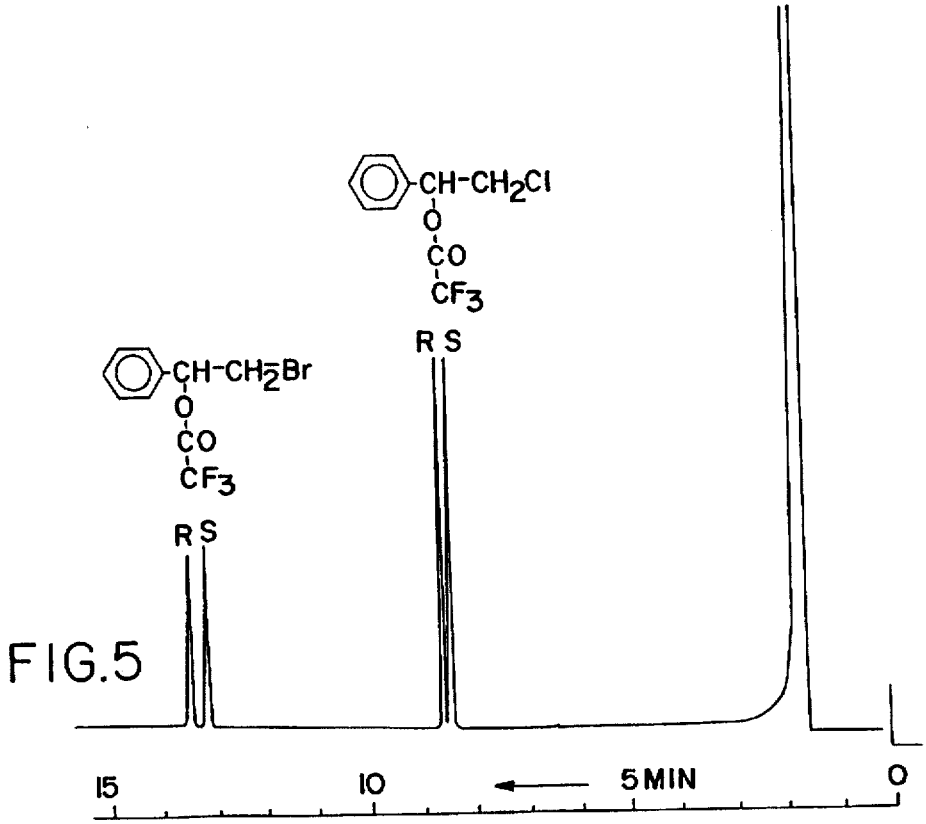

FIG. 5: Separation of enantiomers of 2-chloro-1-phenylethanol and 2-bromo-1-phenylethanol after trifluoroacetylation. 40 m-glass capillary with hexakis(2,3,6-tri-O-pentyl)-α-cyclodextrin, 110° C.

Figure 6:
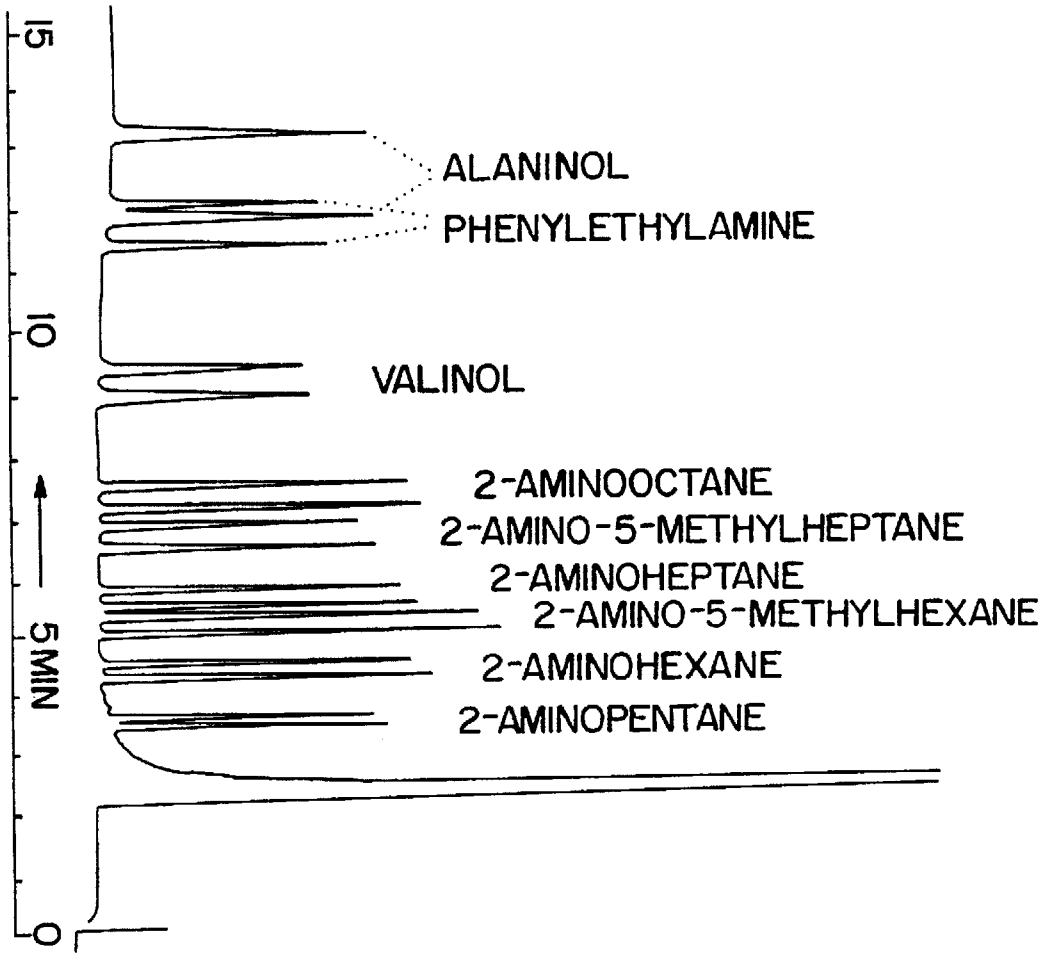

FIG. 6: Separation of enantiomers of amines and amino alcohols after trifluoroacetylation. R-enantiomers are eluted first. 45 m-glass capillary with heptakis(2,6-di-O-pentyl-3-O-acetyl)-β-cyclodextrin; 140° C., 2°/min.

Figure 7:
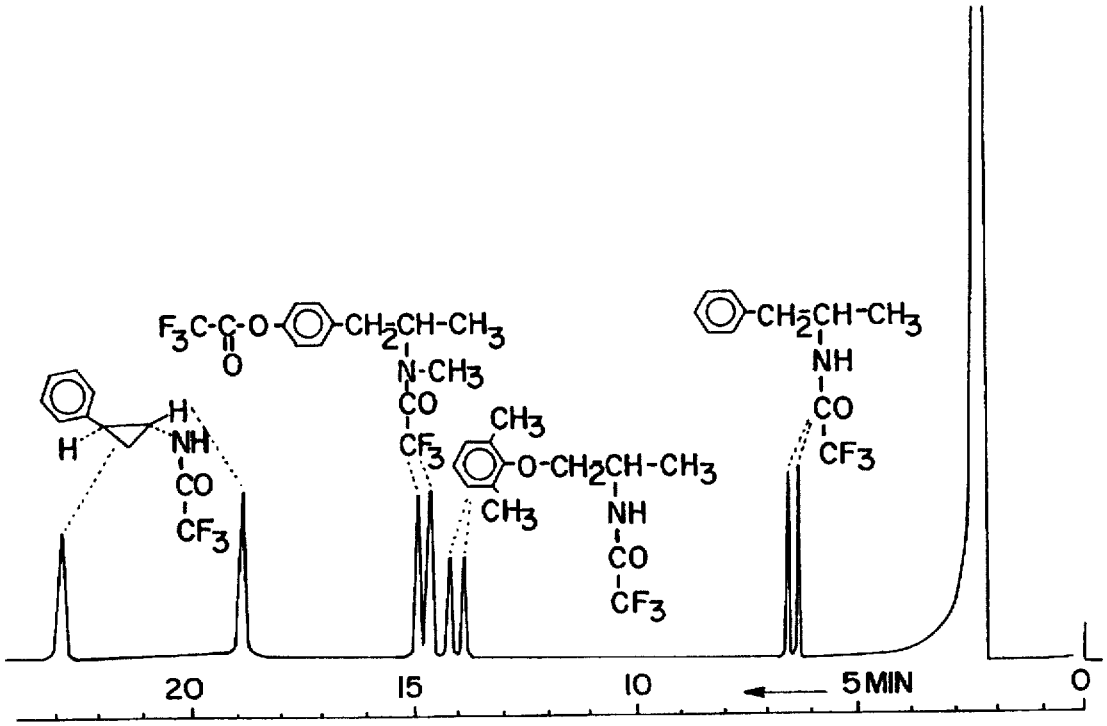

FIG. 7: Separation of enantiomers of chiral pharmaceuticals (amphetamine, mexiletin, pholedrine, tranylcypromine). 45 m-glass capillary with heptakis(2,6-di-O-pentyl-3-O-acetyl)-β-cyclodextrin; 175° C.

Figure 8:
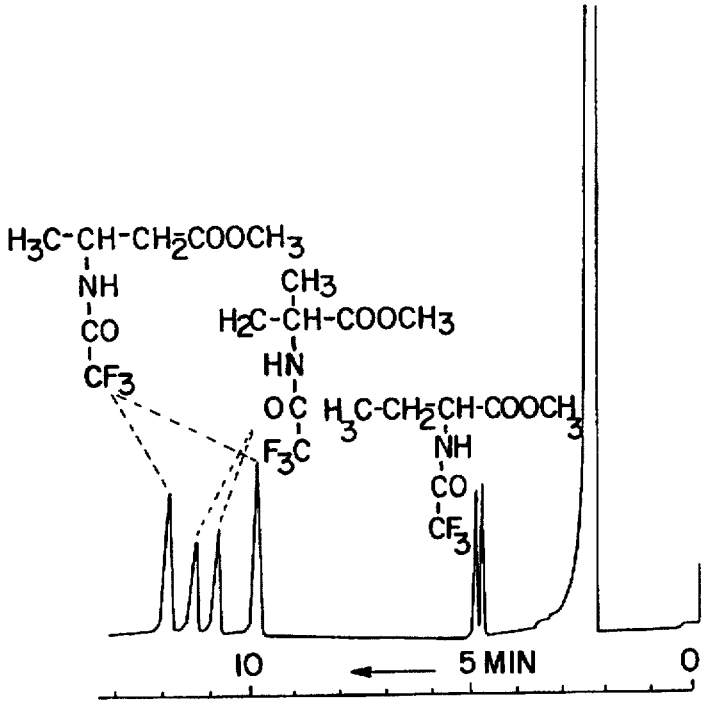

FIG. 8: Separation of enantiomers of α-amino butyric acid, β-amino butyric acid, and β-aminoisobutyric acid after esterification with methanolic HCl and trifluoroacetylation. 45 m-glass capillary with heptakis(2,6-di-O-pentyl-3-O-acetyl)-β-cyclodexttin; 140° C.

Figure 9:
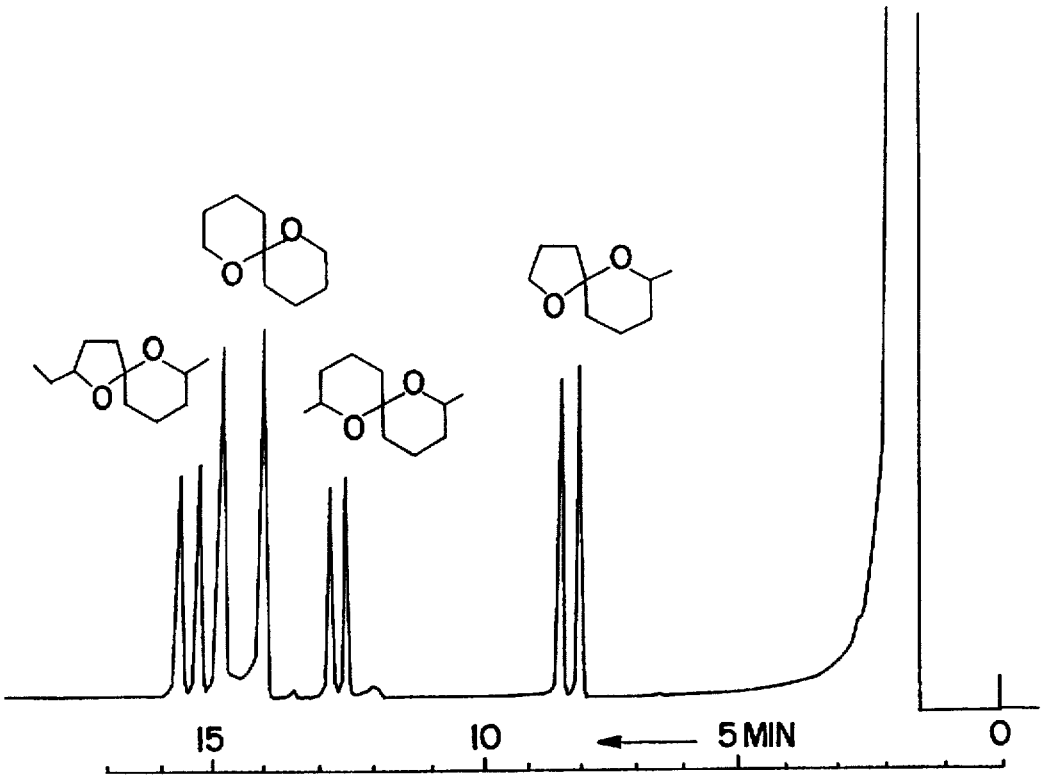

FIG. 9: Separation of enantiomers of spiro-acetals. 40 m-glass capillary with hexakis(2,3,6-tri-O-pentyl)-α-cyclodextrin; 100° C.

Figure 10:
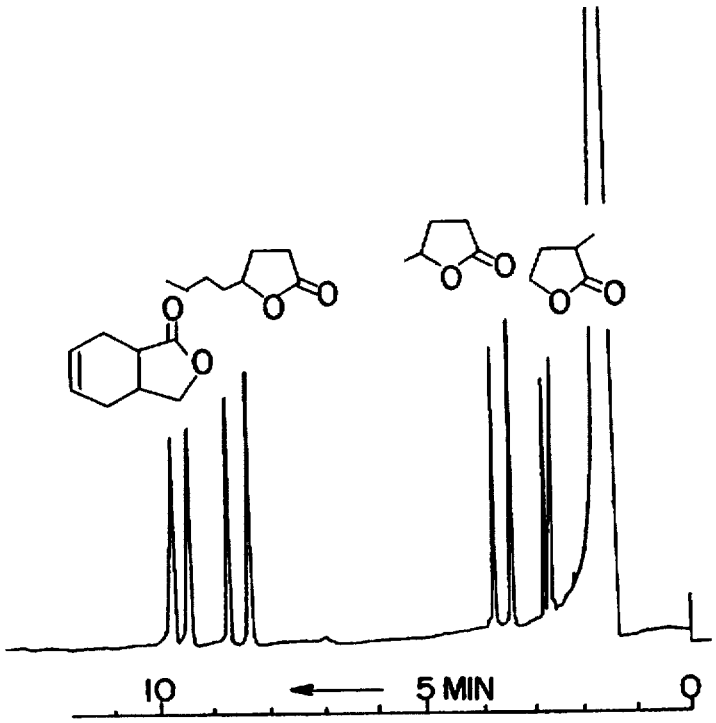

FIG. 10: Separation of enantiomers of γ-lactones, 38 m-glass capillary with hexakis(3-O-acetyl-2,6-di-O-pentyl)-α-cyclodextrin; 150° C.

The invention will be illustrated by the following examples:

EXAMPLE 1

Production of hexakis(2,6-di-O-pentyl)-α-cyclodextrin. 10.5 g (10 mmol) α-cyclodextrin (Consortium für Elektrochemische Industrie, München) [Syndicate for electrochemical industry, Munich] are dissolved in 250 ml dimethyl sulfoxide (Riedel-de Haen) (dried over molecular sieve 4 Å) under protective gas (nitrogen). 14.4 g (360 mmol) powdered sodium hydroxide (Merck) and 54.4 g n-pentylbromide (Fluka) are added thereto and stirred at room temperature. Sedimentation of a white precipitate (sodium bromide) indicates the start of the reaction. During the course of 4 further days, 18.5 g (120 mmol) n-pentylbromide and 4.8 g (120 mmol) sodium hydroxide are each added daily. After a total of 5 days of reaction time, the reaction mixture is poured on 1.5 l water and extracted twice with 500 ml t-butyl-methyl ether. The combined ether phases are washed with water and conc. solution of sodium chloride and are concentrated under vacuum. The residue, a yellow oil, is dried under vacuum (0.05 torr) at 70° C. for 16 hours.

The crude product (15 g) is fractionated by column chromatography over 500 g silica gel Si6O (40–60 μm; Merck). As mobile solvent petroleum ether boilng range 60°–90° C.)/t-butyl-methyl ether are used, blending ratio 70:30 (v/v). The following fractions are obtained:

I 800 ml impurities
II 775 ml pure product
III 700 ml impure product

The volumes of the fractions to some extent depend on the water content of the silica gel. After distilling off the solvent from fraction II and drying under vacuum (0.05 torr) at 70° C., 7.42 g of the pure product in form of a colorless glass are obtained.

$^1$H-NMR-data (Bruker, 300 MHz, internal standard tetramethylsilane, δ-values in toluene-$d_8$): 5.04 ($C_1$—H), 3.37 ($C_2$—H), 4.37 ($C_3$—H), 3.69 ($C_4$—H), 4.00 ($C_5$—H), 3.84 ($C_6$—$H_a$), 4.0 ($C_6$—$H_b$), 3.57 (O—$CH_{2(6)}$), 3.65 (O—$CH_{2(6')}$), 3.57 (O—$CH_{2(2')}$), 4.15 (O—$CH_{2(2)}$), 1.5–1.7 (O—$CH_2$—$\underline{CH_2}$), 1.2–1.4 (O—$CH_2$—$CH_2$—$\underline{CH_2}$), 1.2–1.4 (O—$CH_2$—$CH_2$—$CH_2$—$\underline{CH_2}$), 0.8–1.0 ($CH_3$), 5.33 (OH).

EXAMPLE 2

Hexakis(2,3,6-tri-O-pentyl)-α-cyclodextrin. 10.5 g (10 mmol) α-cyclodextrin are reacted with n-pentyl bromide/ sodium hydroxide according to Example 1. The crude product so obtained is dissolved in 300 ml tetrahydrofuran (Fluka, dried over sodium/benzophenone) under protective gas (nitrogen). This solution is added to 4.3 g (180 mmol) sodium hydride (Fluka, 80% suspension in mineral oil). Adherent mineral oil is removed by washing the sodium hydride with tetrahydrofuran. Subsequently, 27.2 g (180 mmol) n-pentyl bromide (Fluka) are added thereto and reflxed under stirring for 5 days. Then the reaction mixture is poured on 500 ml water, and the tetrahydrofuran is distilled off. The residue is extracted twice with 200 ml t-butyl-methyl ether each. The unified ether phases are washed with water and conc. solution of sodium chloride and boiled down under vacuum. The yellow, oily residue is dried under vacuum (0.05 torr) at 70° C. for 16 hours.

The crude product is fractionated by column chromatography over 500 g silica gel Si6O (Merck, 40–63 μm). As solvent petroleum ether (boiling range 60°–95° C.)/t-butyl-methyl ether are used, blending ratio 85:15 (v/v). The following fractions are obtained:

I 825 ml impurities

II 150 ml pure product (8.0 g)

III 225 ml impure product (5.0 g)

The volumes of the fractions to some extent depend on the water content of the silica gel. By chromatography of fraction III, 2.5 g pure product could once again be obtained. After chromatography, the product is slightly yellowish. After filtration over 50 g aluminum oxide (basic, Merck) with petroleum ether/t-butyl methyl ether 85:15 (v/v) the compound is a transparent, viscous oil.

$^1$H-NMR-data (Bruker, 300 MHz, internal standard tetramethylsilane, δ-values in $CDCl_3$): 5.21 ($C_1$—H), 3.21 ($C_2$—H), 3.59 ($C_3$—H), 3.79 ($C_4$—H), 3.70 ($C_5$—H), 3.45 ($C_6$—$H_a$), 3.98 ($C_6$—$H_b$), 3.35 (O—$CH_{2(6)}$), 3.47 (O—$CH_{2(6')}$), 3.66 (O—$CH_{2(2')}$), 3.95 (O—$CH_{2(2)}$), 3.53 (O—$CH_{2(3)}$), 3.62 (O—$CH_{2(3')}$), 1.5–1.7 (O—$CH_2$—$\underline{CH_2}$), 1.2–1.4 (O—$CH_2$—$CH_2$—$\underline{CH_2}$), 1.2–1.4 (O—$CH_2$—$CH_2$—$CH_2$—$\underline{CH_2}$), 0.8–1.0 ($CH_3$).

EXAMPLE 3

Heptakis(2,6-di-O-pentyl-3-acetyl)-β-cyclodextrin. 1.06 g (0.5 mmol) heptakis(2,6-di-O-pentyl)-β-cycludextrin (produced according to the direction of Exanple 2) are dissolved with 21 mg (0.175 mmol) 4-dimethylamino pyridine (Merck) in 5 ml $CH_2Cl_2$ (Aldrich; dried by distillation over diphosphorus pentaoxide) over nitrogen as protective gas. At first, 0.6 ml (8 mmol) triethylamine (Fluka, dried by distillation over calcium hydride) and subsequently 0.7 ml (7 mmol) acetic anhydride (Fluka) are added thereto. After 24 hours of refluxing, another 0.6 ml (8 mmol) triethylanaine and 0.7 ml (7 mmol) acetic anhydride are added. After 72 hours of reaction, the solvent is removed under water-jet vacuum, and the residue is taken up in 40 ml t-butyl methyl ether (Merck). The organic phase is washed with water, diluted $NaHCO_3$-solution, once again water, diluted $NaH_2PO_4$-solution and water. The organic phase is subsequently concentrated under vacuum, and after drying under vacuum an orange-brown oil is obtained.

The crude product so obtained (0.93 g) is fractionated by chromatography over 35 g silica gel Si60 (Merck, 40–63 μm). As elutung agent dichloromcthane/t-butyl methyl ether 50:50 (v/v) are used. The following fractions are obtained:

I 65 ml impurities

II 40 ml impure product

III 180 ml pure product

After distluing off the solveat and drying, 0.35 g of the pure product is obtained as yellowish glass.

$^1$H-NMR-data (Bruker, 300 MHz, internal standard tetramethylsilane, δ-values in $CDCl_3$): 5.03 ($C_1$—H), 3.26–3.30 ($C_2$—H), 5.18 ($C_3$—H), 3.81 ($C_4$—H), 3.90–3.99 ($C_5$—H and $C_6$—H), 3.36–3.54 ($C_6$,—H, O—$CH_2$(6,), O—$CH_{2(2)}$, O—$CH_{2(2')}$), 1.4–1.59 (O—$CH_2$—$\underline{CH_2}$, O—$CH_2$—$CH_2$—$\underline{CH_2}$), 1.21–1.33 (O—$CH_2$—$CH_2$—$CH_2$—$\underline{CH_2}$), 0.86–0.92 ($CH_3$); 2.05 ($CH_3$—CO).

It is understood that the specification and examples are illustrative but not limitative of the present invention and that other embodiments within the spirit and scope of the invention will suggest themselves to those skilled in the art.

We claim:

1. A substituted cyclodextrin of the formula

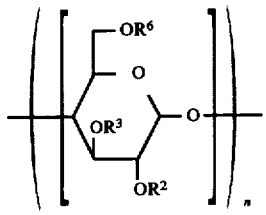

in which $R^2$, $R^3$ and $R^6$ each independently is an alkyl or alkenyl group having 1 to 8 carbon atoms, or a cycloalkyl group having 5 to 8 carbon atoms, or $R^3$ may be an acyl group having 1 to 8 carbon atoms or an acyl group substituted with an aromatic hydrocarbon radical or a saturated or olefinically unsaturated aliphatic or cycloaliphatic radical having 1 to 8 carbon atoms, and n is 6 or 7, with the exclusion of those compounds wherein $R^2$=$R^3$=$R^6$=methyl, n=6 or 7, $R^2$=$R^3$=$R^6$=ethyl, n=7, $R^2$=$R^6$=allyl, $R^3$=methyl, n=7, $R^2$=$R^6$=prop-1-enyl, $R^3$=methyl, n=7, $R^2$=$R_6$=methyl, $R^3$=n-butyl, n=7, $R^2$=$R^6$=methyl, $R^3$=benzoyl, n=7 and $R^2$=$R_3$=alkyl or acyl, $R^6$[=C>4]>$C_4$-alkyl.

2. A substituted cyclodextrin according to claim 1, wherein the alkyl and/or acyl groups have 3 to 6 carbon atoms.

3. A subsututed cyclodextrin according to claim 1, wherein $R^2$, $R^3$ and $R^6$ are alkyl or alkenyl groups with 3 to 6 carbon atoms or $R^3$ may be an acetyl group.

4. A substituted cyclodextrin according to claim 1, wherein $R^2$ and $R^6$ each is e n-pcntyl-group and $R^3$ is an acetyl group.

5. A process for the production of a substituted cyclodextrin according to claim 1, which comprises dissolving an α- or β-cyclodextrin in an anhydrous solvent, adding a pulverted alkali hydroxide, and reacting the cyclodextrin with an alkyl halide.

6. A process according to claim 5, including the further step of reacting the product with an acylating agent in an anhydrous solvent containing an amine.

7. A process according to claim 5 wherein the anhydrous solvent is aprotic.

8. A process according to claim 6 wherein the anhydrous solvent is aprotic.

[9. A process according to claim 6, 7 or 8 wherein the reactions are carried out under inert gas.]

[10. In the chrormatographic separation of individual chiral organic organic compounds from a mixture by contacting the mixture with a stationary phase, the improvement which comprises employing as the stationary phase a substituted cyclodextrin according to claim 1.]

11. A separation process according to claim 10, wherein the contact is made with the chiral organic compounds in gas phase.

12. A separation process according to claim 10, wherein the chiral organic compounds are enantiomers.

13. A separation process according to claim 12, wherein the enantiomers are selected from the group consisting of alcohols, polyols, 1,5-anhydro-alditols; hydroxy esters, aldols, lactones, spiro-acetals, amines, amino-alcohols, amino-acid esters and a trifluoroacetylation product of any of the foregoing.

14. A separation process according to claim 13, wherein the enantiomers are polyols selected from the group consisting of diols, polyols containing more than two hydroxy groups and monosaccharides.

15. A separation process according to claim 14, wherein the enantionmers are methylglycosides.

*16. A process according to claims 5, 6, 7 or 8 wherein the reactions are carried out under inert gas.*

*17. In the chromatographic separation of individual chiral organic compounds from a mixture by contacting the mixture with a stationary phase, the improvement which comprises employing as the stationary phase a substituted cyclodextrin of the formula*

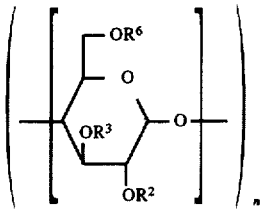

*in which*

*$R^2$, $R^3$ and $R^6$ each independently is an alkyl or alkenyl group having 1 to 8 carbon atoms, or a cycloalkyl group having 5 to 8 carbon atoms, or*

*$R^3$ may be an acyl group having 1 to 8 carbon atoms or an acyl group substituted with an aromatic hydrocarbon radical or a saturated or olefinically unsaturated aliphatic or cycloaliphatic radical having 1 to 8 carbon atoms, and n is 6 or 7,*

*with the exclusion of those compounds wherein*

*$R^2$=$R^3$=$R^6$=methyl, n=6 or 7, and*

*$R^2$=$R^6$=allyl, $R^3$=methyl, n=7, and*

*$R^2$=$R^6$=prop-1-enyl, $R^3$=methyl, n=7, and*

*$R^2$=$R^6$=methyl, $R^3$=n-butyl, n=7.*

* * * * *